United States Patent [19]

Heffernan

[11] 4,187,861
[45] Feb. 12, 1980

[54] BLOOD SAMPLE HANDLING APPARATUS AND METHOD

[76] Inventor: Bart T. Heffernan, 26 Saranac Rd., Sea Ranch Lakes, Fla. 33308

[21] Appl. No.: 879,123

[22] Filed: Feb. 21, 1978

[51] Int. Cl.$^2$ ............................................. A61B 10/00
[52] U.S. Cl. ..................... 128/764; 128/767; 210/DIG. 23
[58] Field of Search ................. 128/DIG. 5, 2 F, 275, 128/276, 214 D; 233/1 R, 1 A, 26; 210/DIG. 23, DIG. 24

[56] References Cited

U.S. PATENT DOCUMENTS

| | | | |
|---|---|---|---|
| 3,211,144 | 10/1965 | Nehring | 128/214 D |
| 3,441,205 | 4/1969 | Young, Jr. | 210/DIG. 23 |
| 3,513,829 | 5/1970 | Deuschle et al. | 128/2 F |
| 3,579,303 | 5/1971 | Pickering | 128/2 W |
| 3,796,542 | 3/1974 | Kline | 128/2 F |
| 3,965,889 | 6/1976 | Sachs | 128/DIG. 5 |

OTHER PUBLICATIONS

Canad. M. A. J., Jul. 1946, vol. 55, pp. 26–30, Jaques et al.

*Primary Examiner*—Robert W. Michell
*Assistant Examiner*—C. F. Rosenbaum
*Attorney, Agent, or Firm*—Malin & Haley

[57] ABSTRACT

An apparatus for handling blood or other material between the time a sample thereof is removed from the patient and the time the sample is presented to the laboratory for placement on a slide or in other test structure for analysis. More specifically, a blood handling container basically cylindrical in shape and rigid enough in construction to be evacuated and with a mid-section that is flexible after filling the container with blood. The flexible section may be chemically different from the end portions or having structurally different shapes such as ribbed support members. Said device being air tight so as to be capable of maintaining a vacuum therein. One or both the ends of said device being composed of a stopper such as rubber or other useful material that is easily pierceable by a hollow needle for filling or discharging. The device is utilized by having the hollow needle placed within but not through the rubber end and then placing the opposite end of the needle in a vein or artery and then forcing the needle through the stopper. The vacuum within the container causes the blood to flow quickly from the vein to the device. The container is then centrifuged separating the blood into two or more components and a specially designed separation means such as a clip is placed on the flexible mid-section of the container to prevent the components from reacting or remixing during transportation.

10 Claims, 8 Drawing Figures

U.S. Patent      Feb. 12, 1980      4,187,861
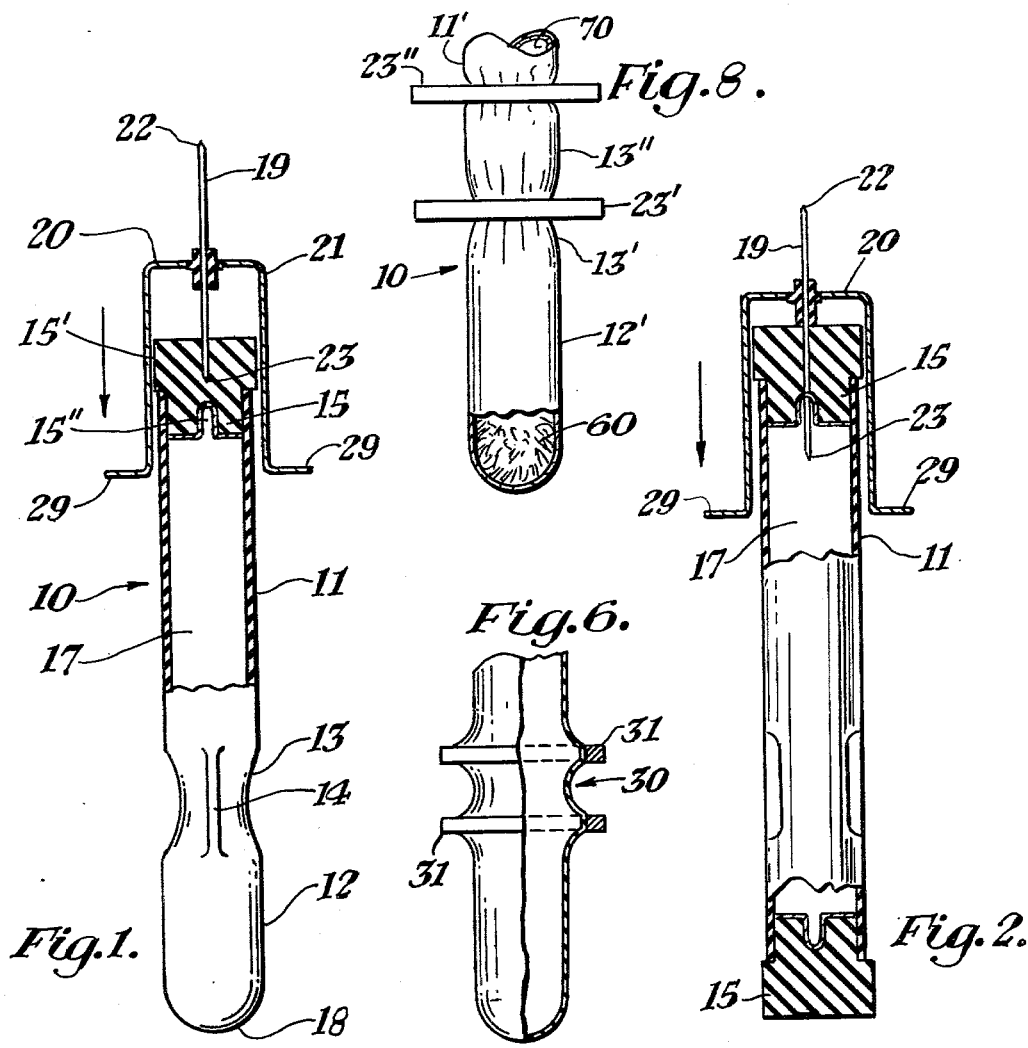
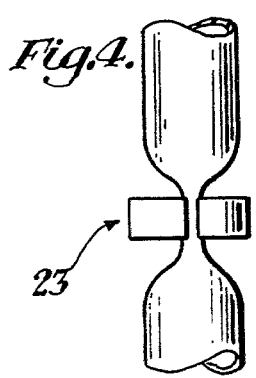
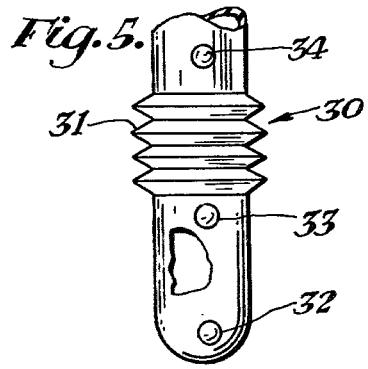
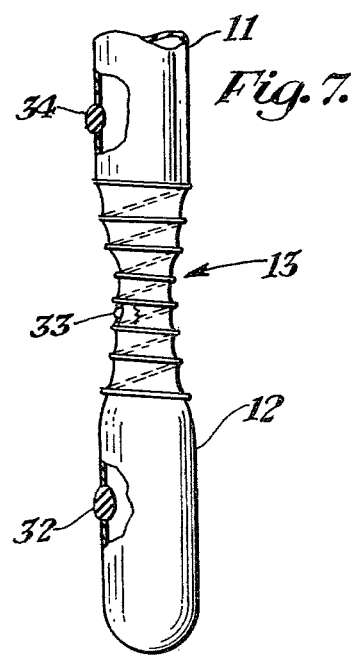
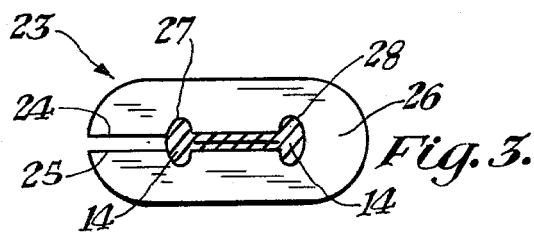

BLOOD SAMPLE HANDLING APPARATUS AND METHOD

BACKGROUND OF THE INVENTION

This invention relates to a method and apparatus for handling blood samples, and more particularly to a device which can be used to withdraw blood or other fluids, hold the blood or fluids while it is centrifuged to separate its components, and which can then be clamped or welded to keep the components separated during transportation.

In modern medicine, the existence of almost every disease, disorder, or condition is ordinarily determined or confirmed by analysis of a sample of blood or other fluids drawn from the patient. Very sophisticated techniques of analysis have been developed and are very effective for this purpose. Typically, in those cases wherein a patient is hospitalized, or presents himself to a well-equipped diagnostic facility, it is common for a blood sample to be taken from the patient at the direction of the physician, and for such sample to be analyzed within a short time after it is taken from the patient.

Ordinarily, a hypodermic syringe is used to pierce the skin and the tip thereof is placed in the vein or artery of the patient, a vacuum is drawn by suitable means to speed filling of the sample container, after a blood sample is taken, the container is subjected to centrifugal force to separate the red cell portion from the plasma portion of the blood. Shortly after this is done, the red blood cell portion or the plasma portion, which are separated from each other by white cells forming the so-called buffy coat, is analyzed according to known techniques. Sometimes, the serum remaining after removal of proteins from the plasma portion is also subjected to analysis. In any case, however, the analysis is ordinarily made within a short time following separation of the blood into these two principal components by centrifugal action. Accordingly, assuming proper test conditions, it is well known that analysis made immediately or very shortly after blood samples are taken is an accurate and very helpful tool for diagnostic or other purposes.

However, blood taken from a patient is, in several important respects, still "alive" in the sense that biological and chemical reactions continue to occur therein even after the blood is removed from the patient. Moreover, it is well known that reactions take place in different portions of blood samples after separation thereof, that is, a factor or characteristic of the red cell and WBC portion of a blood sample may react with a component or element of the plasma or serum portion of the blood. Whereas this condition is a normal one during the time the blood is within the body of the patient, and is not harmful per se, it is a condition which adversely affects the accuracy of blood analysis if the analysis is carried out a significant time after removal of the blood from the body of the patient.

Accordingly, in those cases wherein the patient is not presented for blood sampling to a hospital or other facility having an adequate and readily available laboratory, and wherein it is customary for the blood sample to be taken for analysis, to be centrifugally separated into red blood cell and plasma fractions, and then be stored until pick up by a representative of the laboratory wherein the tests are to be taken, the likelihood of an inaccurate analysis is increased.

Consequently, because of the "live" nature of the blood, analysis performed on blood samples of this type may be inaccurate, useless, or even misleading and perhaps dangerous when used as a diagnostic base for administering treatment to the patient whose blood is analyzed.

In order to avoid this problem a variety of specimen handling devices have been developed, see U.S. Pat. No. 3,579,303 to Pickering, U.S. Pat. No. 3,441,205 to Young, and U.S. Pat. No. 3,838,970 to Kline. These devices suffer from the disadvantage of not being capable of performing the three functions of (1) withdrawing the blood from a vein or artery, (2) holding the blood during centrifugation, and (3) keeping the component parts of the centrifuged blood separated. If the blood must be transferred to other containers before analysis, the chance of contamination is increased, and the procedure becomes more costly and inconvenient to perform. The present invention is a practical solution to many of the problems of the prior art. The present invention may be used to transfer specimens from the device to the test structures.

BRIEF SUMMARY OF THE INVENTION

The present invention device has a shape similar to that of an ordinary test tube. The tube is rigid enough to be evacuated in order to provide the force to withdraw blood from a person. At least the central portion of the tube is flexible enough to allow the tube to be pinched closed. The central portion may possess the flexibility required by structure, design, and/or chemical design. The central portion may be thinner and/or may have longitudinal or concentric ribs in it for support. One end of the tube may be sealed and the other end sealably capped with a rubber stopper or both ends may be capped with stoppers of suitable material. The capped container must be air tight in order to maintain a vacuum within it for a reasonable length of time. Small rubber puncture pods may be placed along the wall of the tube to aid in latter extraction of the blood at various levels after the blood is drawn and centrifuged.

In order to use the device described above, a hollow needle is placed in a stopper at the end of the tube. The needle is so placed that it is securely held in position but does not penetrate to the inside of the container. The positioned needle is then inserted into a vein or artery. The end of the needle in the stopper is then forced into the tube in which the vacuum is maintained. This is accomplished by fixing the position of the needle and then pushing on the distal end of the tube to drive the needle into the tube. The device is rigid in longitudinal compression. The venous blood pressure which is low, if any, is combined with the vacuum force tube to move the blood into the tube. The pressure differential forces the blood into the device. The needle is then withdrawn from the vein or artery and from the stopper. The tube is centrifuged in order to separate the plurality of blood or other material components. A pincher clamp means is actuated or transversely placed on the device to separate the desired number of components. When a pincher clamp is used it may be designed to conform to the longitudinal or concentric ribs, if any, on the flexible central portion. The clamp or sealing of the walls together prevents the blood components from thereafter interacting.

In accordance with the above described structure and operation, it is the primary object of this invention to facilitate ready and accurate analysis of blood samples by providing a device which can prevent interaction between the elements of blood or other material in one separated fraction thereof and elements in another or second, separated fraction.

Another object is to provide a method and apparatus including a device for receiving a blood or other specimens, for facilitating separation of blood on a gravitational basis, and for maintaining a separation between the two or more layers of blood or other material components so as to minimize reaction therebetween.

Still another object is to provide a device that may be evacuated for later use and thereafter adapted to maintain the separate identity of two or more blood fractions and which is simple and reliable to operate, and which is low in cost.

A still further object is to provide a device which may be used with or forms a part of an apparatus for obtaining a blood sample and which may be used as the original specimen gathering vessel, as the centrifuged vessel to separate blood fractions in the vessel and as a vessel for isolating the separated fractions from each and storing the separated fractions during the time between separation and subsequent analysis.

Another object is to provide a processing device which includes means for receiving a specimen of blood and a means for effecting a physical barrier between fractions of blood which have been separated.

A still further object is to provide an apparatus which includes an exterior, relatively rigid support unit, a flexible center section and a separator adapted for use over the flexible center element so as to provide a barrier between the separated blood fractions which may be maintained until analysis is carried out.

Another object is to provide a blood sampling apparatus having simple and effective means for facilitating the rapid filling of the sample container.

Another object is to provide a blood sampling apparatus that is designed to provide means to move material out of the vessel onto or into test areas for performing material tests.

Still a further object is to provide a blood sampling apparatus which is adapted to safe and sanitary use, and which prevents contamination of the samples and minimizes risks for the patient.

Yet another object is to provide such a device with a puncturable wall to allow for the easy removal of blood from various levels of the device.

Still another object is to present such a device which has its inner surface textured so as to prevent clotting in certain areas of the device and promotes it in others.

Another object is to provide a blood handling apparatus having one or more of the foregoing advantages and characteristics, and which is simple in use and economical and reliable to operate.

Other objects and advantages of the invention, and the manner of their attainment, will become more clear when reference is made to the following detailed description of the preferred embodiments of the invention set forth by way of example, and shown in the accompanying drawings, wherein like reference numbers indicate corresponding parts throughout.

BRIEF DESCRIPTION OF THE DRAWINGS

FIG. 1 is a partial vertical sectional view of the apparatus with ancillary needle and holder illustrated.

FIG. 2 is a partial vertical sectional view of another embodiment of the apparatus with ancillary needle and holder illustrated.

FIG. 3 is a plane view of the specially designed pincher clamp holding the flexible portion of the tube.

FIG. 4 is an enlarged perspective view of the flexible center portion of the device with the clamp in place.

FIG. 5 is a collapsed view of a third embodiment showing accordian pleating of a thinner wall at a flexible center portion.

FIG. 6 is another view of FIG. 5 with the flexible center portion expanded.

FIG. 7 is a fourth embodiment showing a spiral accordion pleating.

FIG. 8 is an illustration showing the container with a plurality of pincher clamps for containerizing more than two compartments and partially in cross-sectional view illustrating a plurality of coatings within the container.

DETAILED DESCRIPTION OF PREFERRED EMBODIMENTS OF THE INVENTION

Before the present blood handling apparatus is specifically described, it is to be understood that the invention is not limited to the particular arrangement of the parts here shown, as such devices may vary. It is also to be understood that the phraseology or terminology herein used is for purposes of description of particular embodiments and not of limitation, as the scope of the present invention is denoted by the appended claims.

Referring now to the drawings, and to FIG. 1 in particular, the device or container generally referred to by the numeral 10, is shown in a partial vertical sectional view. The device 10 has cylindrical walls 11 on its upper portion, and similar cylindrical walls 12 on its lower portion. The upper walls 11 are connected to the lower walls 12 by a flexible middle section 13 having a multiplicity of longitudinal ribs 14 thereon, or as described herein below. The ribs provide longitudinal strength. A rubber plug 15 includes shelf 15'. The plug 15 has a cavity 15" in its center to allow the plug to be easily penetrated by a needle. The plug is sealably connected to wall 11 at its top. The other end 18 of the device 10 is formed by a continuation and intersection of the walls 12. A vacuum is created in the interior 17 before or after the stopper 15 is fixed into place in any well known manner. In order to make use of the device 10, a hollow needle 19 may be used to allow blood to flow into the vacuum. The needle 19 may be used with a needle holder having a radially extending wall portion 20 and an axially extending side wall portion 21 which has a finger gripping flange portion 29. Both ends 22 and 23 of needle 19 are sharpened. It should be noted that the end 18 may also be sealed by a plug 15 as shown in FIG. 2.

The device may be of a single thickness of material having strength enough in at least the upper portion 11 and lower portion 12 to hold a vacuum of 1 to 2 psi above a complete vacuum and at the same time would allow a pincher clamp to divide the inside of the device or container.

The pincher clamp generally referred to by the numeral 23 is shown in FIGS. 3 and 4. The clamp 23 has opposing surfaces 24 and 25 which are connected via a biasing hinge means 26 which force the two surfaces 24 and 25 toward each to press opposite side of the container wall into contact with one another. FIG. 3 shows the clamp in a closed position holding the flexible portion of the tube. The notches 27 and 28 along the edge surfaces 24 and 25 serve to receive the longitudinal ribs 14, thus making it possible for the clamp 23 to squeeze opposite walls of the flexible center portion 13 together so tightly as to completely separate the upper and lower portions of the device 10. A clamp or a plurality of clamps such as 31, 23' and 23" without the notches may be designed for use on a device or container shown in FIGS. 5, 6, 7, or 8.

FIGS. 5 and 6 show another embodiment with a flexible mid-portion 30 between portions 11 and 12. The flexible section 30 in FIG. 5 has transverse accordion pleats 31 which run concentrically around the device. FIG. 5 shows the accordion section expanded. This construction also provides suitable results as do other obvious modifications thereon. When using a device as in FIG. 5, the blood may be removed by placing a hollow needle (not shown) through any of the rubber side plugs 32, 33, or 34 and then squeezing the ends of the device to compress the accordion pleats to the position shown in FIG. 5, the force creates pressure to force the separated portions of the blood out of the device. It may be desirable to use a hollow needle with a filter (not shown) in the exiting blood flow path.

It should be noted that it is desirable to treat the inner surface of the wall 11 as shown in FIG. 8 with a suitable non-thromboplastic coating 70 such as silicone to prevent clotting. The lower inside wall of portion 12' may be roughened or include a fiberglass projection into the container as shown at 60 to promote clotting of the blood component that settles at the bottom of the device.

FIG. 7 illustrates a spiral accordion shaped mid-portion 13. Puncture pods 32, 33, and 34 may be located at any position in the wall, 11, 12 or in the flexible position 13 as shown in FIG. 7. Puncture pods may be used to extract material at different levels by using a needle.

Referring again to FIG. 8, shows the flexible midportion clamp by two separate clamps 23' and 23". This clamping provides three separated volumes of fluid in the device. Such clamping will allow the area 13" to be cut while maintaining the closed integrity of portions 11' and 12'.

In order to use the device, an evacuated container 10 is chosen. A container as shown in the FIGS. 5, 7, or 8 will be chosen if the user will later want to perform tests on various components of the blood. When the appropriate device is chosen, a hollow needle 19 having extensions 20, 21, and 29 is partially inserted into the rubber stopper 15. The point 22 of the needle is then inserted into a vein or artery (not shown). A force F is then applied to the flange portion 29 of extension 21 forcing the point 23 of needle 19 into the evacuated chamber 17. Due to the pressure differential between the blood in the vein in which point 22 is, and the evacuated chamber 17 in which point 23 is, the blood in the vein will rush into the chamber 17. The needle 19 is then completely removed from the stopper 15; due to the resilience of the stopper the hole made by needle 19 will seal itself. The device is then centrifuged in order to separate the components of blood. After separation of the blood's components, the clamp 23 or a clamp without notches is placed on the flexible middle portion 13 as shown in FIGS. 4, 6, or 8. The notches 27 and 28 should fit over the longitudinal ribs 14 if the device shown in FIG. 1 is used. With the clamp properly placed on the device, two blood components are separated and the device may be stored or shipped without the mixing of, or reaction between components. When tests are to be made of the blood's components, a needle may be inserted into either compartment of the container via stoppers 15 so that the blood may be withdrawn or through the various puncture pods as is shown in FIGS. 5 and 7. A syringe may be used to withdraw blood from the device via puncture pods 32, 33, or 34.

A plurality of clamps on the devices without notches, may be used to separate more than two blood components as shown in FIG. 8.

When accordion pleated mid portion is used, the device may be used to dispense fluid from the device by moving portion 11 toward portion 12.

The instant invention has been shown and described herein in what is considered to be the most practical and preferred embodiments. It is recognized, however, that departures may be made therefrom within the scope of the invention as claimed and that obvious modifications will occur to a person skilled in the art.

What I claim is:

1. A specimen handling device, comprising:
   a body,
   a first relatively rigid body portion, said first body portion being shaped and structured having a first volume within said first portion, said first body portion including an entrance, said first body portion constructed of material to provide a said first volume that may be evacuated,
   a second relatively rigid body portion connected to said first body portion, said second body portion being shaped and structured having a second volume, said second body portion constructed of material to provide a said second volume that may be evacuated,
   at least one mid portion connected between said first body portion and said second body portion and providing an operable connection between said first volume and said second volume, each said mid portion having flexible walls movable toward one another for sealing shut and separating said first volume from said second volume, and
   a first means for sealing shut said entrance, said first means composed of a resilient material whereby at least a portion of said walls lie in contact with adjacent walls when said first volume and said second volume are evacuated, and when clamping means are connected across said mid portion it will separate said first volume of said first body portion from said second volume of said second body portion.

2. A specimen handling device as recited in claim 1, wherein:
   said first body portion is coated on its inner surface with a non-thromboplastic coating.

3. A specimen handling device as in claim 1, wherein:
   said mid portion has a multiplicity of longitudinal ribs.

4. A specimen handling device as in claim 1, wherein:
   said mid portion is composed of a thin flexible material.

5. A specimen handling device as in claim 2, wherein:
   said mid portion has an accordion shape.

6. A specimen handling device as in claim 1, wherein:
   said second body portion has an inner surface which has been roughened.

7. A specimen handling device as in claim 1, further comprising a multiplicity of puncture pods in said first body portion; said second body portion and said mid portion.

8. A method of handling specimens utilizing a device including a first and second body portions shaped and sized to hold an evacuated volume with a flexible collapsible mid portion that is collapsed when the first and second body portions are evacuated, and a pierceable cap, comprising the steps of:

inserting a hollow needle partially into said cap,
inserting said hollow needle into a vein or artery, and
forcing said hollow needle completely through said cap into said device and allowing blood to flow into said body portion,
withdrawing said hollow needle completely from the vein or artery and from said cap,
centrifuging said device to separate the blood,
placing at least one hand manipulated clamp on said mid portion to separate portion of the blood.

9. A method as set forth in claim 8 including the steps of:

inserting a hollow needle into at least one of the body portions and compressing the device to distribute the sample to laboratory test areas from the same device that originally received the blood.

10. A method as set forth in claim 8 including the step of:

cutting the device on one side of a clamp to allow shipment of only a particular portion of the separated blood.

* * * * *